United States Patent
Cowan et al.

(10) Patent No.: US 7,632,245 B1
(45) Date of Patent: Dec. 15, 2009

(54) DEVICES, SYSTEMS AND METHODS FOR DELIVERY OF A FLUID INTO A PATIENT DURING A MAGNETIC RESONANCE PROCEDURE

(75) Inventors: Kevin P. Cowan, Allison Park, PA (US); Frederick W. Trombley, III, Pittsburgh, PA (US); David M. Reilly, Pittsburgh, PA (US); David M. Griffiths, Pittsburgh, PA (US); George J. Misic, Pittsburgh, PA (US); Keith Callan, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/921,083

(22) Filed: Aug. 18, 2004

Related U.S. Application Data

(60) Provisional application No. 60/495,972, filed on Aug. 18, 2003.

(51) Int. Cl.
*A61M 5/19* (2006.01)
(52) U.S. Cl. .................. 604/131; 600/420; 600/431; 600/432
(58) Field of Classification Search .......... 600/413, 600/892.1, 410, 420, 431, 432; D24/112; 604/131–157, 246–250; 424/9.3
See application file for complete search history.

(56) References Cited

U.S. PATENT DOCUMENTS

| | | | |
|---|---|---|---|
| 4,006,736 A | | 2/1977 | Kranys et al. |
| 4,367,737 A | * | 1/1983 | Kozam et al. ............ 604/191 |
| 4,677,980 A | | 7/1987 | Reilly et al. |
| 4,936,315 A | * | 6/1990 | Lineback ................. 600/578 |
| 5,033,650 A | * | 7/1991 | Colin et al. .............. 222/137 |
| 5,176,642 A | * | 1/1993 | Clement .................. 604/135 |

(Continued)

FOREIGN PATENT DOCUMENTS

JP    2002035125 A  *  2/2002

(Continued)

OTHER PUBLICATIONS

Keeler, E.K., "Accessory Equipment Considerations with Respect to MRI Compatibility," JMRI, 8, 1 (1998).

(Continued)

*Primary Examiner*—Brian Casler
*Assistant Examiner*—Parikha S Mehta
(74) *Attorney, Agent, or Firm*—James R. Stevenson; Gregory L. Bradley

(57) ABSTRACT

A device for injection of a fluid into a patient includes a container adapted to hold the fluid and defining an outlet through which the fluid can exit the container. A pressurizing mechanism is in connection with the container for pressurizing the fluid, and an actuator is in fluid connection with the outlet. The actuator has a first state in which fluid is prevented from flowing through the outlet and a second state in which fluid can flow through the outlet. The injection device further includes a flow regulator to control the flow rate of fluid in fluid connection with the outlet. The container, the pressurizing mechanism, the actuator and the flow regulator can be MR compatible, thereby making the device suitable for use in or near the bore of an MR scanner.

25 Claims, 10 Drawing Sheets

U.S. PATENT DOCUMENTS

| | | | |
|---|---|---|---|
| 5,279,608 A * | 1/1994 | Cherif Cheikh | 604/892.1 |
| 5,312,389 A * | 5/1994 | Theeuwes et al. | 604/892.1 |
| 5,383,858 A | 1/1995 | Reilly et al. | |
| 5,494,036 A | 2/1996 | Uber, III et al. | |
| 5,553,619 A * | 9/1996 | Prince | 600/420 |
| 5,588,556 A | 12/1996 | Sancoff et al. | |
| 5,746,208 A * | 5/1998 | Prince | 600/420 |
| 5,911,252 A * | 6/1999 | Cassel | 141/234 |
| RE37,602 E * | 3/2002 | Uber et al. | 600/432 |
| 6,387,228 B1 | 5/2002 | Maget | |
| 6,413,238 B1 | 7/2002 | Maget | |
| 6,656,157 B1 * | 12/2003 | Duchon et al. | 604/131 |
| 6,704,592 B1 | 3/2004 | Reynolds et al. | |
| 6,923,800 B2 * | 8/2005 | Chen et al. | 604/892.1 |
| 7,221,159 B2 | 5/2007 | Griffiths et al. | |
| 2001/0056233 A1 * | 12/2001 | Uber et al. | 600/431 |
| 2002/0017484 A1 * | 2/2002 | Dourdeville | 210/198.2 |
| 2002/0107481 A1 * | 8/2002 | Reilly et al. | 604/152 |
| 2002/0115933 A1 * | 8/2002 | Duchon et al. | 600/432 |
| 2003/0199787 A1 * | 10/2003 | Schwindt | 600/568 |
| 2003/0236442 A1 * | 12/2003 | Connors et al. | 600/29 |
| 2004/0030233 A1 | 2/2004 | Frazier et al. | |
| 2004/0171983 A1 * | 9/2004 | Sparks et al. | 604/65 |
| 2004/0181147 A1 * | 9/2004 | Prince | 600/420 |
| 2004/0193045 A1 * | 9/2004 | Scarborough et al. | 600/432 |
| 2005/0070848 A1 * | 3/2005 | Kim et al. | 604/140 |
| 2005/0107738 A1 * | 5/2005 | Slater et al. | 604/96.01 |
| 2005/0197531 A1 * | 9/2005 | Cabiri et al. | 600/116 |
| 2005/0209790 A1 * | 9/2005 | Niethammer | 702/28 |

FOREIGN PATENT DOCUMENTS

| | | |
|---|---|---|
| WO | 0192907 | 12/2001 |

OTHER PUBLICATIONS

Lemieux, L. et al., "Recording of EEG During MRI Experiments: Patient Safety," MRM, 38, 943 (1997).

"A Primer on Medical Device Interactions with Magnetic Resonance Imaging Systems," U.S. Food and Drug Administration—Center for Devices and Radiological Health (Feb. 7, 1997).

U.S. Appl. No. 10/916,946, filed Aug. 12, 2004, Griffiths et al.

* cited by examiner

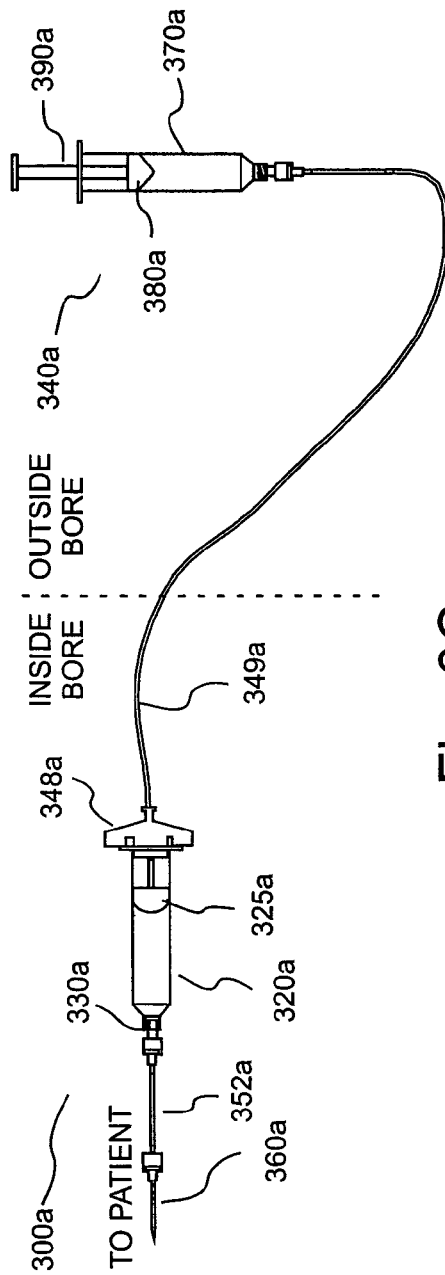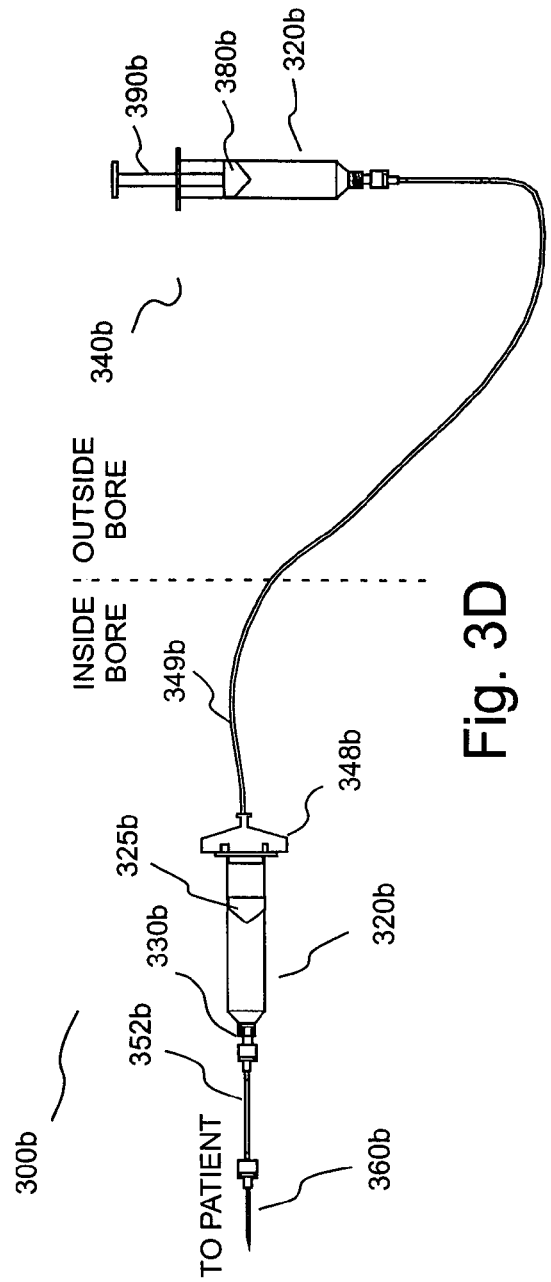

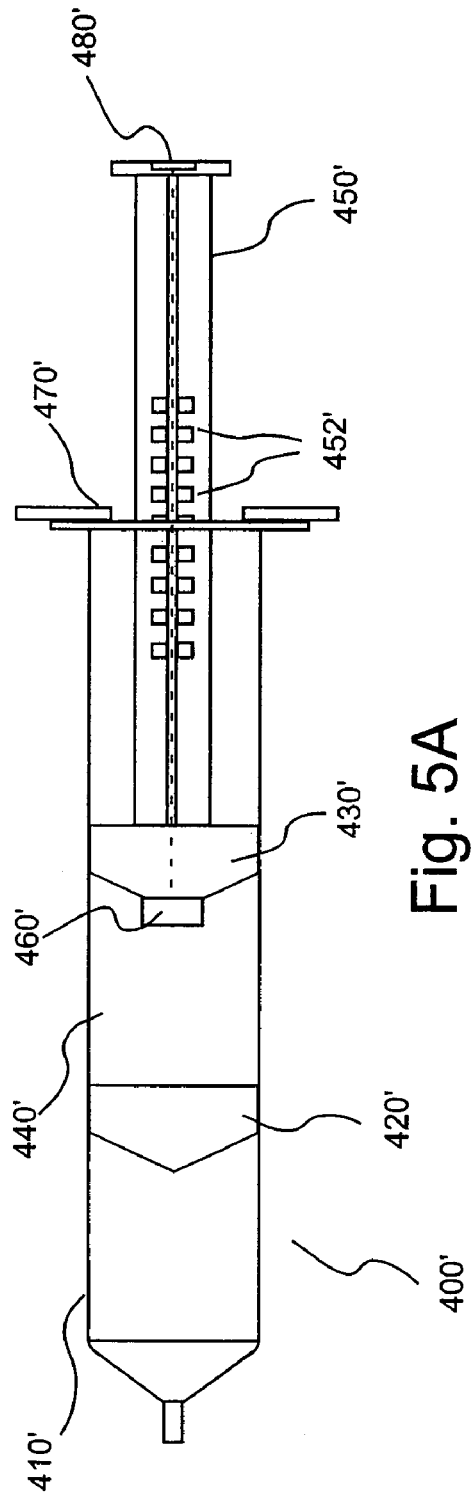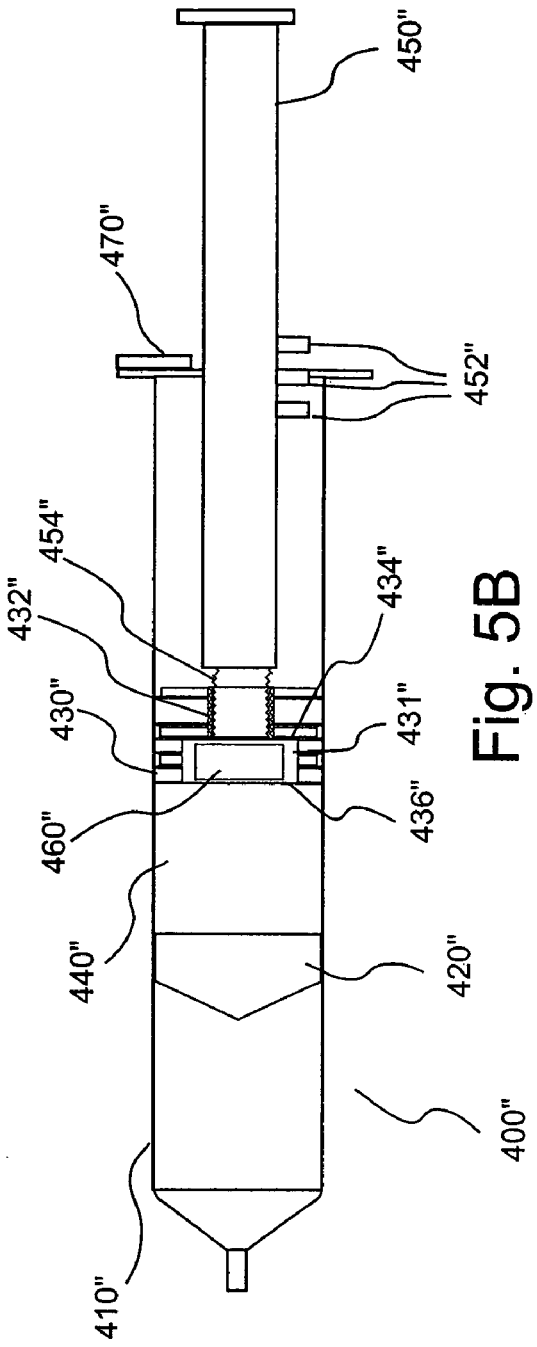
Fig. 5A
Fig. 5B

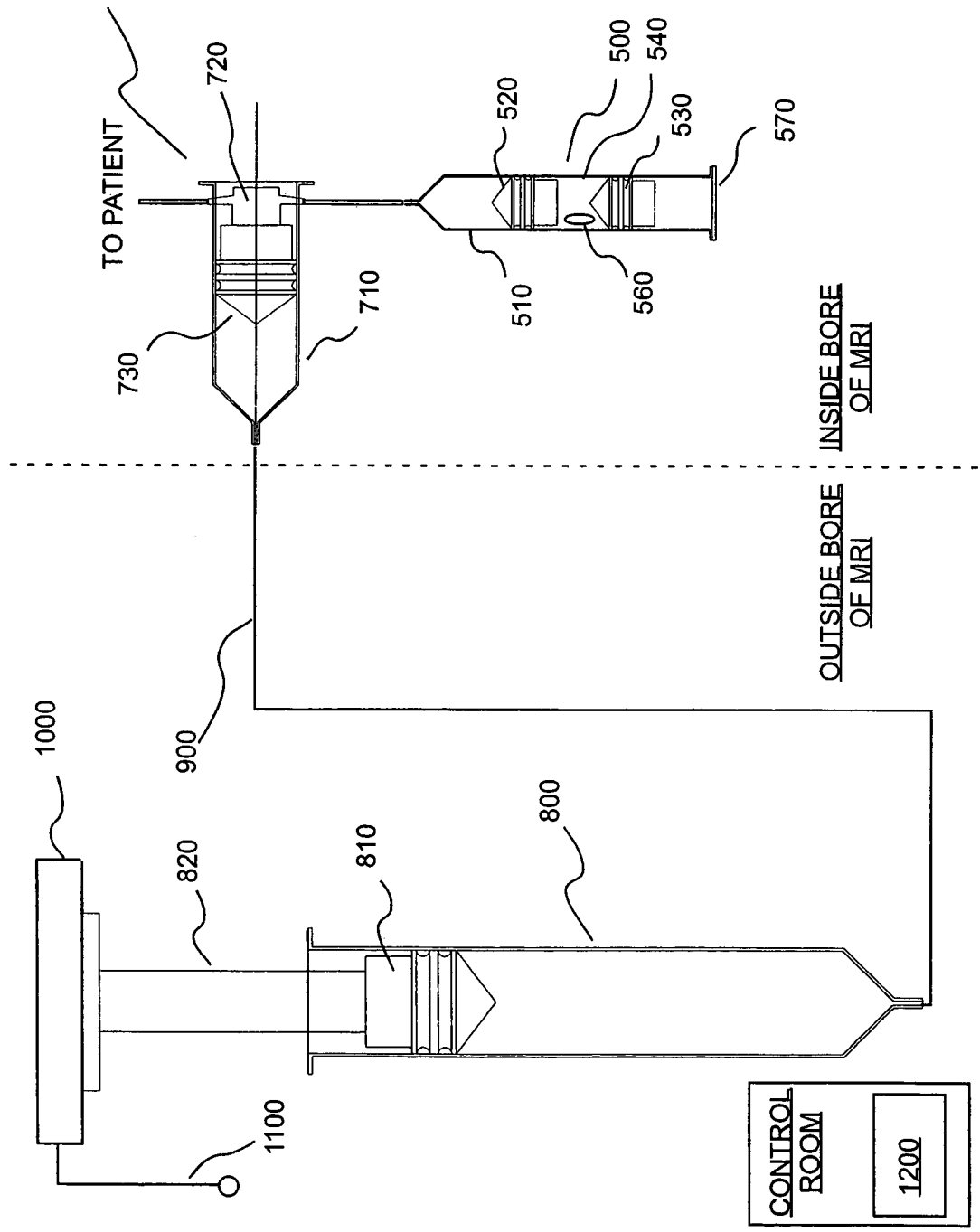

DEVICES, SYSTEMS AND METHODS FOR DELIVERY OF A FLUID INTO A PATIENT DURING A MAGNETIC RESONANCE PROCEDURE

CROSS-REFERENCE TO RELATED APPLICATIONS

This application claims the benefit of U.S. Provisional Application Ser. No. 60/495,972, filed on Aug. 18, 2003, the contents of which are incorporated herein by reference. This application is also related to U.S. application Ser. No. 10/916,946, filed on Aug. 12, 2004, titled "Actuators And Fluid Delivery Systems Using Such Actuators."

BACKGROUND OF THE INVENTION

The present invention relates generally to devices, systems and methods for delivery of a fluid, and, particularly, for infusion or injection of a fluid into a patient.

A number of injector-actuated syringes and powered injectors for use in medical procedures such as angiography, computed tomography (CT), ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

Although significant advances have been made in the design and operation of powered injectors, a number of problems persist which can limit their use. For example, each year in the United States several million MRI procedures are performed. However, powered injectors are used in only a relatively small percentage of such procedures. In MRI procedures in which there is no need to accurately control the timing of contrast injection or the flow rate of injection, powered injectors are almost never used. In that regard, MRI procedures are relatively expensive and patient throughput is a primary concern. It is perceived that use of powered injectors in such procedures will require additional time, while providing little benefit. Thus, in contrast-enhanced procedure in which timing and flow rate control are not important, contrast is currently injected manually. Typically, the patient is placed in the MRI bore and a baseline scan is performed. The patient is then removed from the bore of the imaging device and the contrast is injected. The patient is then once again placed in the bore and the contrast-enhanced imaging is performed.

A number of problems often arise with the manual injection of contrast in an MRI procedure. For example, after injection it is often difficult to reposition the patient in the same position in which the baseline measurement was made. Even if repositioning can be achieved with success, removal of the patient from the bore to manually inject contrast and subsequent repositioning require a substantial amount of time. Moreover, in some instances, particularly with claustrophobic patients, the patient refuses to reenter the bore. Furthermore, it is sometimes difficult with some patients to properly inject the contrast manually. In such cases, it may become necessary to call for the services of an IV specialist team, greatly increasing the amount of time required for the scan.

Even in imaging procedures other than MRI procedures (such as CT, angiography and ultrasound), there may be reluctance to use powered injectors in certain procedures because of perceived or actual burdens with such use.

For the above reasons and others, it is desirable to develop improved devices, systems and methods for the injection of fluids into patients.

SUMMARY OF THE INVENTION

In one aspect, the present invention provides a device for injection of a fluid into a patient, including: a container to hold fluid, the container comprising an outlet through which fluid can exit the container, a pressurizing mechanism in connection with the container for pressurizing the fluid, and an actuator in fluid connection with the outlet. The actuator has a first state in which pressurized fluid is prevented from flowing through the outlet and a second state in which pressurized fluid can flow through the outlet. The injection device further includes a flow regulator to control the flow rate of fluid in fluid connection with the outlet.

In one embodiment, the container is a syringe with a plunger slidably disposed therein, and the pressurizing mechanism is in operative connection with the plunger.

The pressurizing mechanism can, for example, be powered by a vacuum drive, a chemical reaction, electrical power, expansion of a compressed gas, spring force or gravity. The mechanism of the actuator can, for example, include a rotory valve, a pinch valve with tubing, a ratchet valve, a fusible link, a trumpet valve, a port closing valve, a pump system or a drive system. The mechanism can, for example, be powered by a vacuum drive, a piezoelectric drive, an electric motor drive, a solenoid drive, an electro resistive pump, a charged ion pump, a magneto restrictive material, a thermochemically activated motion (TCAM®) device, a shape memory alloy (SMA) such as nitenol (a nickel-titanium alloy), a state transition, a bi-metallic material, an electro-active polymeric material or gravity. A number of non-magnetic, electroactive actuators (and fluid delivery systems) suitable for use in the present invention are described in U.S. Provisional Patent Application No. 60/495,386, entitled Actuators and Fluid Delivery Systems Using such Actuators, filed Aug. 15, 2003, assigned the assignee of the present invention, the disclosure of which is incorporated herein by reference.

The injection device can also include a controller to control the state of the actuator. The controller can be remote from the actuator. The controller can, for example, be untethered from the actuator. The controller can, for example, control the state of the actuator via ultrasound, via a protocol of an imaging scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via optical light, an RF signal, or via line power.

In one embodiment, the container, the pressurizing mechanism, the actuator and the flow regulator are MR compatible, thereby making the device suitable for use in or near the bore of an MR scanner.

The regulator can, for example, include a fluid path element of a known diameter. For example, the regulator can be an orifice or a catheter. Multiple orifices or an adjustable orifice can be provided for multiple flow rates. As used herein, the term "orifice" refers to an opening through which a fluid can pass and is typically a stricture or narrowing in the flow path providing a restriction to flow. A restriction to flow can also be created by adjustment (for example, lengthening) of the fluid path. Flow rate can also be controlled by controlling the pressure generated by the pressurizing mechanism.

The injection device can also include an attachment mechanism for attaching the device to the patient.

In one embodiment, the pressurizing mechanism includes a vacuum drive in operative connection with syringe plunger. The vacuum drive can include at least one chamber with a sealing member slidably disposed therein, wherein at least a partial vacuum is created by drawing the sealing member through the chamber. The pressurizing mechanism can also include a pressurized gas in operative connection with the syringe plunger. In one embodiment, the gas is a product of a chemical reaction. In another embodiment, the gas is supplied from a storage tank.

In another aspect, the present invention provides a system for use in magnetic resonance imaging, including: a magnetic resonance scanner comprising a bore in which a patient is positioned for a scan and a device for injection of a fluid in a patient. As described above, the device includes a container to hold fluid. The container includes an outlet through which fluid can exit the container. The injection device further includes a pressurizing mechanism in connection with the container for pressurizing the fluid. An actuator is in fluid connection with the outlet. The actuator has a first state in which pressurized fluid is prevented from flowing through the outlet and a second state in which pressurized fluid can flow through the outlet. The injection device further includes a flow regulator to control the flow rate of fluid in fluid connection with the outlet.

Preferably, the container, the pressurizing mechanism, the actuator and the flow regulator are MR compatible, thereby making the device suitable for use in or near the bore of an MR scanner.

In another aspect, the present invention provides a method of injection of a fluid into a patient including the steps: (i) attaching a container to hold fluid to the patient, the container including an outlet through which fluid can exit the container; a pressurizing mechanism being in connection with the container for pressurizing the fluid, and (ii) controlling an actuator in fluid connection with the outlet to be in a second state, the actuator having a first state in which pressurized fluid is prevented from flowing through the outlet and the second state in which pressurized fluid can flow through the outlet.

The step of controlling an actuator can occur remote from the patient. The patient can, for example, be inside the bore of an MR scanner and the controller for controlling the actuator can be remote from the patient.

In another aspect, the present invention provides a method of injecting a fluid into a patient during an MR procedure including the steps: (i) placing a container to hold fluid in close vicinity of the patient, the container including an outlet through which a fluid can exit the container, a pressurizing mechanism being in connection with the container to pressurize the fluid, and (ii) remotely controlling an actuator in fluid connection with the outlet to be in a second state, the actuator having a first state in which pressurized fluid is prevented from flowing through the outlet and the second state in which pressurized fluid can flow through the outlet.

The container can be MR compatible and be within the bore of the MR scanner. The container can, for example, be attached to the patient within the bore of the MR scanner.

In another aspect, the present invention provides a method performing an MR scan, including the steps: (i) placing an MR compatible container to hold contrast fluid in close vicinity or proximity to the patient, the container including an outlet through which contrast fluid can exit the container, a pressurizing mechanism being in connection with the container for pressurizing the fluid, (ii) performing a baseline scan, and injecting a contrast fluid into the patient without removing the patient from the bore of the MR scanner by controlling an actuator in fluid connection with the outlet to be in a second state, the actuator having a first state in which pressurized fluid is prevented from flowing through the outlet and the second state in which pressurized fluid can flow through the outlet. The container can be within the bore of the MR scanner. The container can also be attached to the patient within the bore of the MR scanner.

In a further aspect, the present invention provides an injection device for use in connection with a syringe having a plunger slidably disposed therein. The injection device includes a plurality of chambers that are closed on one end. Each chamber has a sealing member slidably disposed therein. At least a partial vacuum is created by drawing the sealing members through the chambers. The sealing members are in operative connection with the force transfer member to transfer force to the plunger of the syringe. The device can further include a cradle for the syringe into which the syringe is removably placed to place the force transfer member in operative connection with the plunger of the syringe.

In one embodiment, the force transfer member includes a connection member in operative connection with the sealing member of the chambers. The connection member includes an attachment member to which a plunger extension, which extends rearward from the plunger of the syringe, is attachable.

In still a further aspect, the present invention provides an injection device including a syringe barrel. The syringe barrel includes a first plunger slideably disposed therein and a second plunger slidably disposed therein. The first plunger is spaced forward from the second plunger in the syringe to create an intermediate volume therebetween. The intermediate volume includes therein a pressurizing mechanism for increasing the pressure in the intermediate volume upon activation of the pressurizing mechanism. The intermediate volume further includes a fluid therein. The pressurizing mechanism can, for example, generate a gas upon activation thereof to increase the pressure in the intermediate volume.

The injection device can further include a plunger extension operatively connected to the second plunger. In one embodiment, the injection device includes a stop mechanism to fix the position of the second plunger. The stop mechanism can, for example, include tabs on the plunger extension that abut with a stop member of the injection device to prevent movement of the injection device. In another embodiment, the plunger extension can be removable from connection with the second plunger and the injection device further includes a seal to close the rearward end of the syringe barrel after the plunger extension has been removed. It is not necessary, however, to seal the rearward end of the syringe barrel. As long as the second plunger is prevented from exiting the rear of the syringe, the injection device will be operable. Thus the injection device can alternatively include an abutment member that prevents the second plunger from exiting the rearward end of the syringe.

In a further embodiment, the plunger extension is axially movable relative to the second plunger to expel a material contained within a chamber of the plunger so that the material contacts a fluid in the intermediate volume with which the material reacts to generate a gas. The plunger can, for example, include threading, and the forward end of the plunger extension can include cooperating threading. In this embodiment, the plunger extension is rotated relative to the plunger to cause the plunger extension to move axially forward relative to the plunger. The axial forward motion of the plunger extension can, for example, force the material through a membrane separating the chamber of the plunger from the fluid within the intermediate volume. In one embodiment, rotation of the plunger extension also fixes the axial position of the second plunger within the syringe by bringing at least one contact member on the plunger into abutting engagement with at least one abutment member on the syringe.

In still a further aspect, the present invention provides an actuator for remote initiation of an injection procedure as described above. The actuator includes a fluid-filled (as used herein, the term fluid refers generally to either a gas or a liquid) chamber in fluid connection with a controller via a length of tubing. The controller is operable to increase the pressure within the chamber upon actuation thereof. The chamber is in operative connection with a valve mechanism that is a normally close state. Increasing fluid pressure in the chamber (via the controller) acts to place the valve in an open state. In one embodiment, the valve mechanism is within the chamber and is separated from the fluid therein by an elastomeric material that moves upon increasing the pressure of the fluid in the chamber to place the valve mechanism in an open state.

Numerous advantages are afforded by the injection devices of the present invention. For example, the devices are readily made patient wearable and readily fabricated to be fully in-bore compatible for MR procedures. The devices of the present invention can, for example, be applied to a patient outside the scanning room, and there is no need to remove a patient from the scanner bore to perform an injection. Likewise, the amount of time required for set up of the devices of the present invention is minimal. The devices of the present invention are also readily adaptable for remote activation, for example, from a scan control room. These advantages and others result in less time required for MR and other procedures and increase patient throughput.

Given the proximity of placement of the devices of the present invention to the patient, no saline flush to remove expensive contrast medium from the fluid path is required as is often necessary with current powered injectors in which long lengths of connective tubing are required. Indeed, in many embodiments of the present invention, less than three inches of connective tubing is required. Preferably, no more than one foot of connective tubing is required between the injection devices of the present invention and the injection point on the patient. The devices of the present invention are inexpensively and readily manufactured from relatively inexpensive materials and can be disposed of on a per-patient and/or other periodic basis, potentially reducing the risk of cross-contamination and making sterilization unnecessary.

Injection fluid (for example, contrast medium, stress agents, saline, blood pool agents and/or organ specific agents) can be delivered to the patient through standard catheters (for example, a 24 gauge butterfly catheter) using the devices of the present invention. Moreover, many of the devices of the present invention are operable with commercially available syringes, which can be supplied empty or prefilled.

BRIEF DESCRIPTION OF THE DRAWINGS

Other aspects of the invention and their advantages will be discerned from the following detailed description when read in connection with the accompanying drawings, in which:

FIG. 3C illustrates another embodiment of an injection device of the present invention.

FIG. 3D illustrates another embodiment of an injection device of the present invention.

FIG. 5A illustrates another embodiment of an injection device of the present invention.

FIG. 5B illustrates another embodiment of an injection device of the present invention.

FIG. 7 illustrates an embodiment of a hydraulic or pneumatic actuation device of the present invention.

DETAILED DESCRIPTION OF THE INVENTION

In general, the present invention provides infusion or injection devices and systems that are relatively easy to operate. The injection devices are preferably readily portable and can even be patient wearable.

Figure 1:
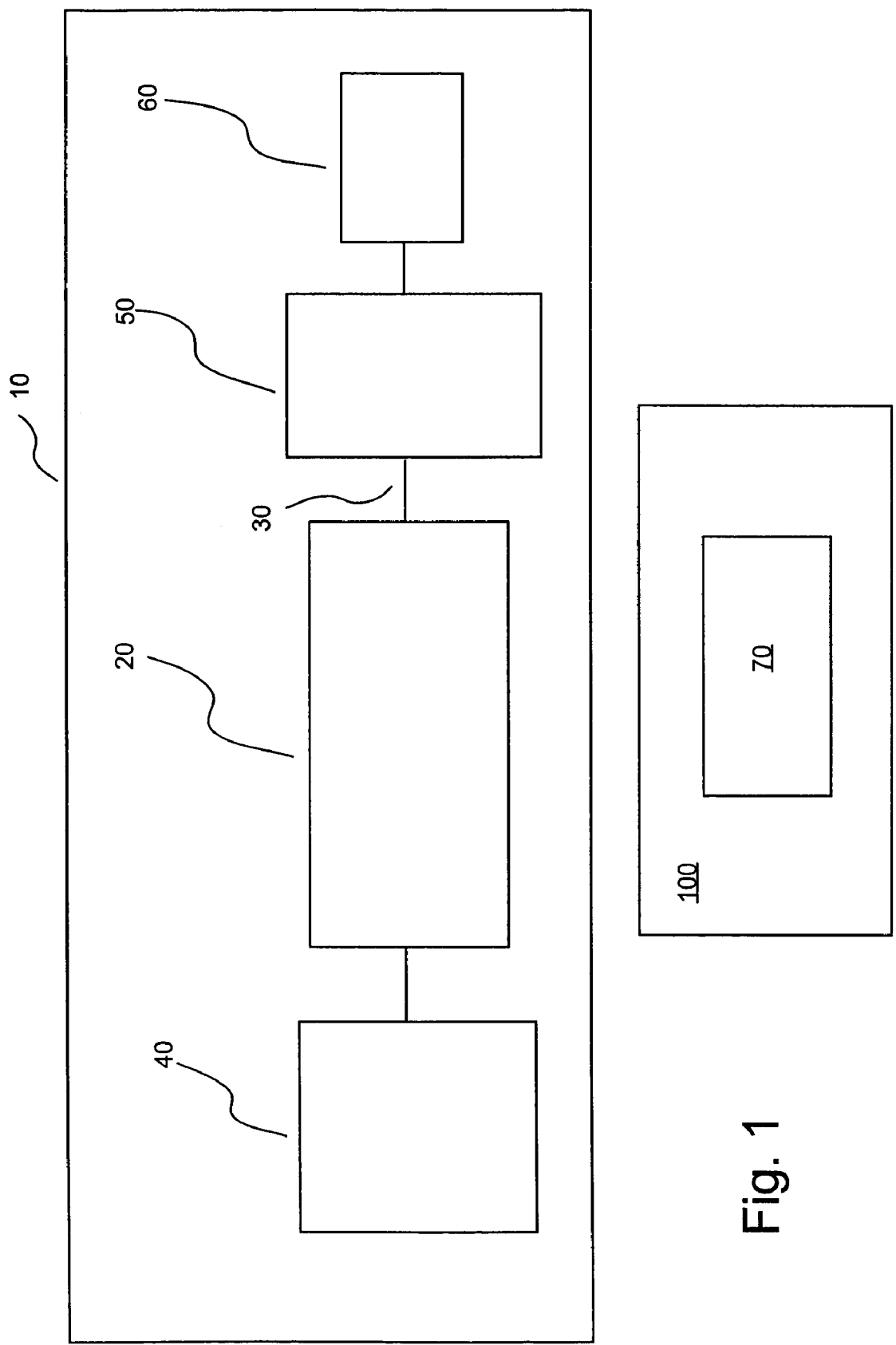
FIG. 1 illustrates a schematic diagram of an injection or infusion device and system of the present invention.

In the embodiment of the present invention illustrated in FIG. 1, an injection or infusion device 10 includes a storage container or chamber 20 (for example, a prefilled syringe) in which a fluid for injection into a patient is stored. Injection device 10 includes an outlet 30 in fluid connection with chamber 20 and through which fluid exits chamber 20 to be injected into the patient. Injection device 10 also includes a pressurizing mechanism 40 through which force/pressure is applied to the fluid within chamber 20 to cause the pressurized fluid to exit outlet 30. Injection device 10 further includes an actuator 50 to initiate (and, possibly, terminate) flow. Actuator 50 can, for example, be remotely operated via a controller from, for example, control room 100. Device 10 further preferably includes a flow controller 60 to regulate the flow rate of fluid into the patient. Flow controller 60 can, for example, include a relatively short length of tubing, or other conduit of known diameter. For example, in one embodiment, the patient catheter (for example, a 24 gauge butterfly catheter) serves as a flow controller. Additionally or alternatively an orifice of a known diameter can be provided as a flow controller. Orifices of different diameters can be provided to create different flow rates. Likewise, an adjustable orifice can be provided for multiple flow rates.

Pressurizing mechanism 40 can provide the force to pressurize the fluid in container or chamber 20 via, for example, air displacement of a vacuum (a vacuum drive), a chemical reaction (for example, releasing an expanding gas), electro-chemical reactions, electrical power (for example, from a battery, wall outlet or from the scanner), expansion of a compressed gas (for example, $CO_2$ or air pressure); spring force or gravity.

Actuator 50 can, for example, include a rotory valve at a syringe tip, a pinch valve w/tubing, a ratchet valve, a fusible link, a trumpet valve, a port closing valve, a pump system or a drive system to allow fluid to flow through outlet 30. The mechanism for operating actuator 50 (or imparting motion thereto to change a state) can, for example, include a vacuum drive, a piezoelectric drive, an electric motor drive (for example, an inside-MRI bore air core motor in which the magnet of the bore forms part of the motor), a solenoid drive, an electric motor drive outside of the bore, an electro resistive pump, a charged ion pump (available, for example, from Exigent), a magneto restrictive material (to which a voltage is applied), a thermochemical activated motion (TCAM) material or device, a nitenol material, a state transition (liquid to gas), a bi-metallic material (with different rates of expansion for each metal), an electro-active polymeric material, and/or gravity. Power can be supplied via, for example, vacuum power, chemical power, electrical power (for example, battery power, wall outlet power), power from the scanner, human/manual power, compressed or pressurized gas (for example, $CO_2$ or air) power; spring power, gravity power, or light/photoelectric power.

Controller 70 can for example, control the state of actuator 50 via ultrasound (for example, via a piezo tweeter operating through glass); via a scanner coil protocol (for example, GE/Siemens scanners comprise approximately 85% of the axial market and include two 15 volt connections); via microwave energy (for example, a glass smart link); via a mechanical or cable link (for example, via a simple string of via camera-type cable link using a plastic cable); via infrared light; via fiber optic cable; via pneumatic power; via hydraulic power; via patient operation; via voice activation; via movement of table 210; via time delay; via an RF gradient trigger from scanner (for example, 5th shim tune); via a photo cell; via optical light control; via line power (for example, via audio frequency through panel); via an RF link, or via operator manual control (that is, sending the operator into the MRI room to activate the device).

For use in an MR environment, the components of injection device 10 are preferably fabricated from materials that are non-magnetic and/or otherwise suitable or compatible for use in an MRI environment. A review of issues related to the compatibility of various equipment in an MRI environment is set forth in Keeler, E. K. et al., "Accessory Equipment Considerations with Respect to MRI Compatibility," *JMRI*, 8, 1 (1998), the disclosure of which is incorporated herein by reference. See also, Lemieux, L. et al., "Recording of EEG During MRI Experiments: Patient Safety," *MRM*, 38, 943 (1997); and "A Primer on Medical Device Interactions with Magnetic Resonance Imaging Systems," U.S Food and Drug Administration—Center for Devices and Radiological Health (Feb. 7, 1997), the disclosures of which are incorporated herein by reference.

In general, many devices, including but not limited to many injectors and infusion pumps, that contain electric actuators such as DC brush motors, step motors, brushless DC motors or other wound coil motors and solenoids often fail in a strong magnetic field as a result of damage to internal permanent magnets. Moreover, currents induced within the field windings of such devices from electromagnetic fields can cause overheating and potential damage to the windings and any connected electronic circuitry. The MRI magnetic field can also interfere with the device created magnetic field and prevent accurate operation.

Furthermore, differences in magnetic permeability of materials within the actuator and eddy currents induced within actuator windings can affect the homogeneity or uniformity of the MRI magnetic field, generating image artifacts. Actuators that use mechanical commutation, such as DC brush motors, can also generate radio frequency energy during switching which can induce unwanted artifacts upon the acquired MRI images.

Figure 2A:
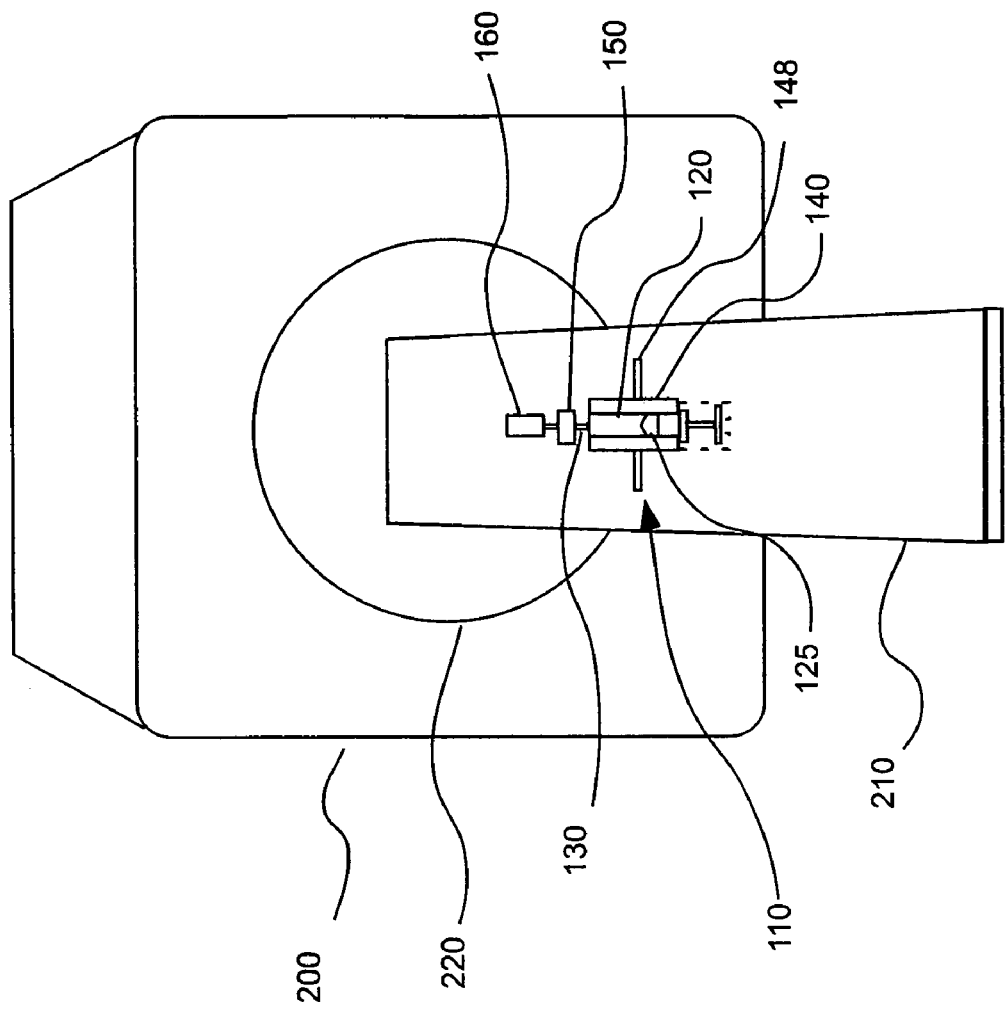
FIG. 2A illustrates one embodiment of an injection device and system of the present invention in an MR environment.
Figure 2A:
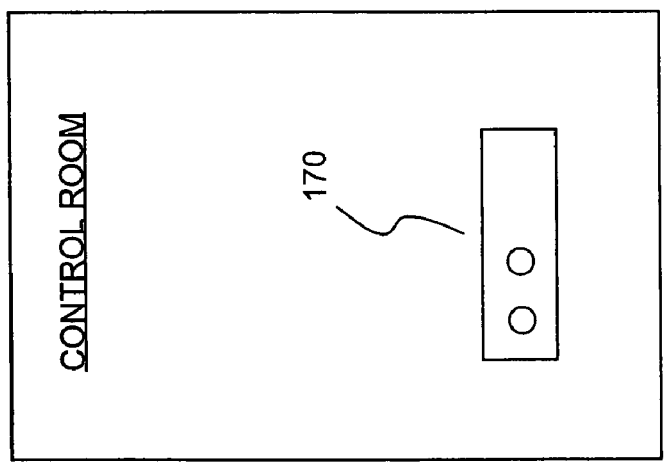
Figure 2B:
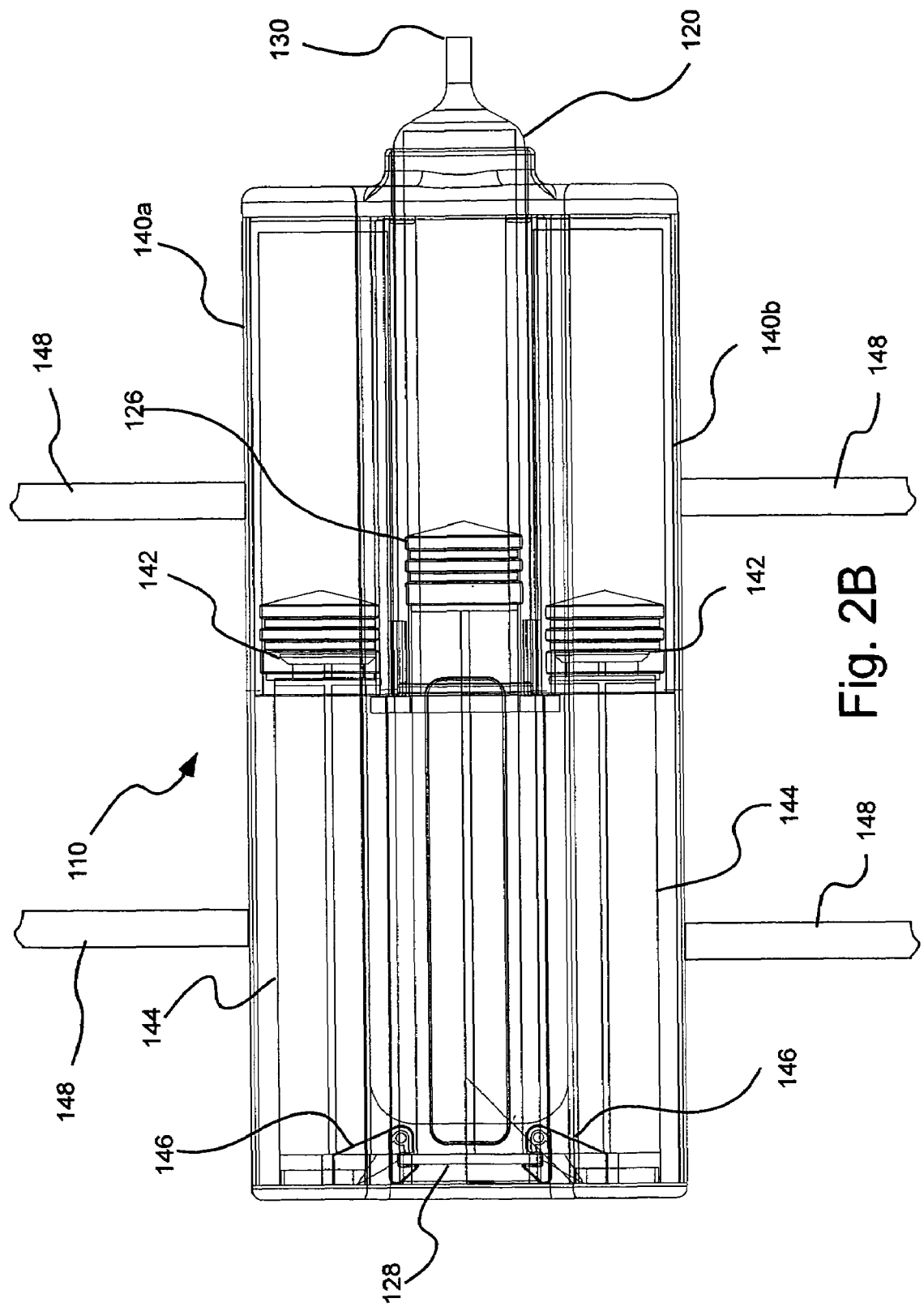
FIG. 2B illustrates an enlarged side view of the injection device of the system of FIG. 2A.

As illustrated in FIGS. 2A and 2B, one embodiment of an injection device 110 of the present invention can be used to inject fluid into the patient (not shown, but positioned on table 210 during an MRI procedure) within or within close proximity of the bore 220 of an MR Scanner 200.

Preferably, the injection devices of the present invention are suitable to be placed within one foot of the MRI bore. More preferably, the injection devices of the present invention are suitable to be placed within the bore, thereby providing close access to the injection site on the patient and eliminating lengthy connective tubing used with many currently available injection devices. In general, to be "MR compatible" as that phrase is used herein, the materials of device 110 should not interfere with the operation of MR scanner 200 in a substantial manner (for example, to cause image artifacts). Additionally, the MR environment (for example, the powerful magnetic field) should not substantially interfere with the operation of injection device 110. Examples of suitable MRI compatible materials for injection device 110 include, but are not limited to, polymeric materials, glass materials and aluminum.

Container or chamber 120 for the injection fluid (generally an MR contrast fluid) can, for example, be a polymeric or glass MR syringe available, for example, from Medrad, Inc. of Indianola, Pa. Such syringes can be purchased "prefilled" with injection fluid or can be purchased empty and filled at the MRI site. The fluid in such syringes is pressurized via a plunger 125, which is slidably disposed within the syringe barrel.

In the embodiment of FIGS. 2A and 2B, pressurizing mechanism 140 includes one or more chambers (for example, syringe barrels 140a and 140b with no outlets or closed ends—see FIG. 2B) in which a vacuum or at least a partial vacuum can be created by for example drawing back a sealing member or members such as a plungers 142. Allowing, for example, air at atmospheric pressure to drive sealing members 142 forward within syringe barrels 140a and 140b to displace or destroy the (partial) vacuum created within syringe chambers 140a and 140b will result in a generally constant force which can be transferred to plunger 126 via mechanical connection(s) as known in the art (for example, via mechanical connection of the sealing member(s) 142 of pressurizing mechanism 140 to a plunger extension 128). As illustrated in FIG. 2B, sealing members 142 can be connected to extending members 144 which are mechanically connected to plunger extension 128 via connectors 146. As extension 144 and plunger extension 128 are drawn rearward, a vacuum is created in syringe chambers 140a and 140b and fluid is drawn into syringe 120. Syringe 120 can thereby be filled and syringe vaccuum chambers 140a and 140b can thereby be "primed" by an operator before a procedure. Alternatively, device 110 can be shipped with syringe 120 prefilled and syringe vacuum chambers 140 "preprimed." Likewise, device 110 can alternatively be shipped with syringe vacuum chambers 140a and 140b preprimed and a prefilled syringe installed on location.

While actuator 150 is in an "off" state, fluid cannot be injected through syringe outlet 130 and sealing members 142 cannot move forward within syringe vacuum chambers 140a and 140b. In that regard, the fluid within syringe 120 is generally incompressible and extensions 144 are mechanically connected to plunger extension 128. Once actuator 150 is placed in an "on" state, fluid can flow through syringe outlet 130 and atmospheric pressure will force sealing members 142 (and thereby extensions 144) to move forward. The force created (which is proportion to atmospheric pressure multiplied by the area of the sealing members) is transferred from extensions 144 to plunger extension 128 and, thus, to plunger 126, thereby forcing pressurized fluid through syringe outlet 130 to be injected into the patient through catheter 160.

Injection device 110 can, for example, be worn by the patient via straps 148. Likewise, device 10 can be attached to scan table 210.

The pressure at which the fluid is injected and the flow rate of fluid to be injected can be controlled, in part, by the diameter of syringe 120 and the diameter of syringe vacuum chambers 140a and 140b. In a typical MR procedure, approximately 15 to 20 ml of MR contrast are injected. To inject approximately 1 mL/sec of the MR contrast MAGNEVIST® (gadopentetate dimeglumine) available from Berlex Laboratories, Inc. of Montville, N.J. through a 24 gauge butterfly catheter requires a pressure of about 30 psi. Vacuum drive pressure mechanism 140 is well suited to provide such pressures and greater pressures.

As set forth above, pressurized fluid flows through outlet 130 upon activation of actuator 150. In the embodiment of FIG. 2A, controller 170 can, for example, activate actuator 150 in a remote, wireless or untethered manner. Whether controller 170 communicates with actuator 150 in an untethered or tethered (for example, via cabling), such communication is preferably MR compatible as described above. Communication in an MR environment suitable for communication between controller 170 and actuator 150 are described, for example, in U.S. Pat. No. 5,494,036 or in U.S. patent application Ser. Nos. 09/586,140, 10/622,242, 10/064, 846 and WO 01/92907, assigned to the assignee of the present invention, the disclosure of which is incorporated herein by reference.

Figure 3A:
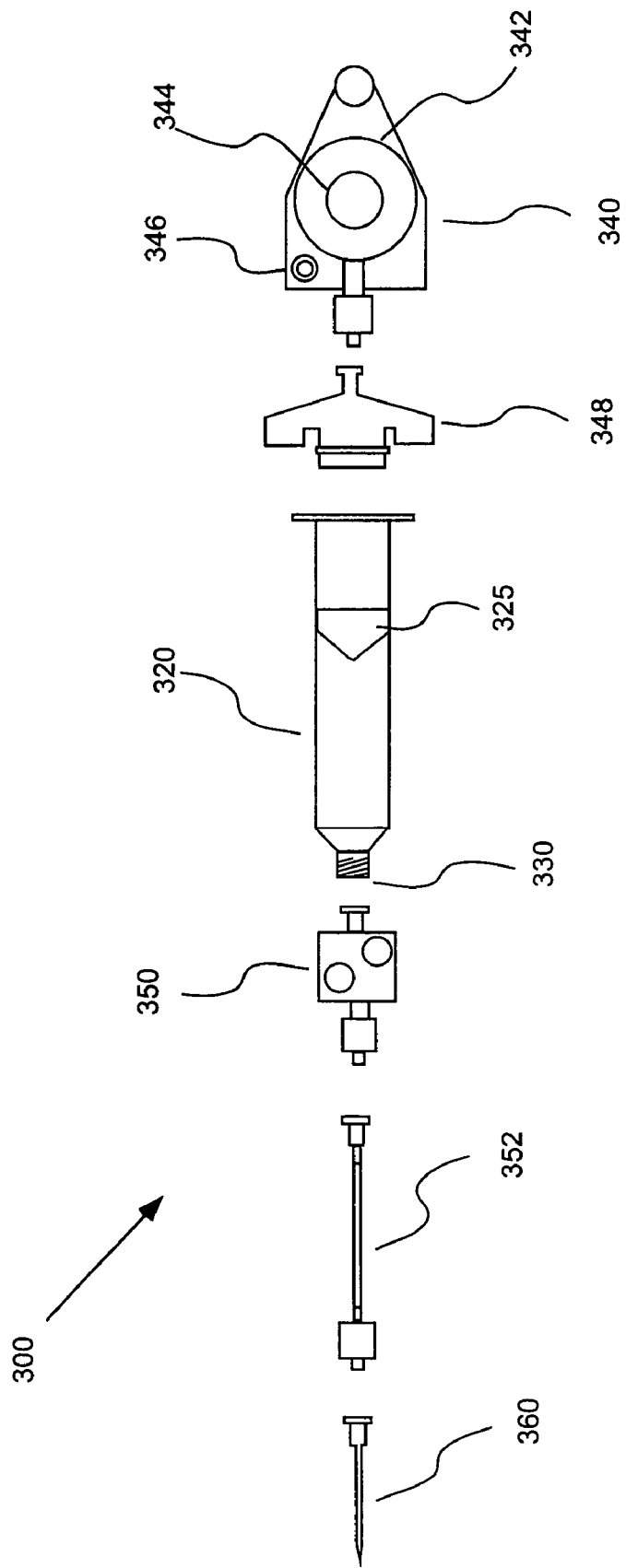
FIG. 3A illustrates another embodiment of an injection device of the present invention in a disassembled or exploded state.
Figure 3B:
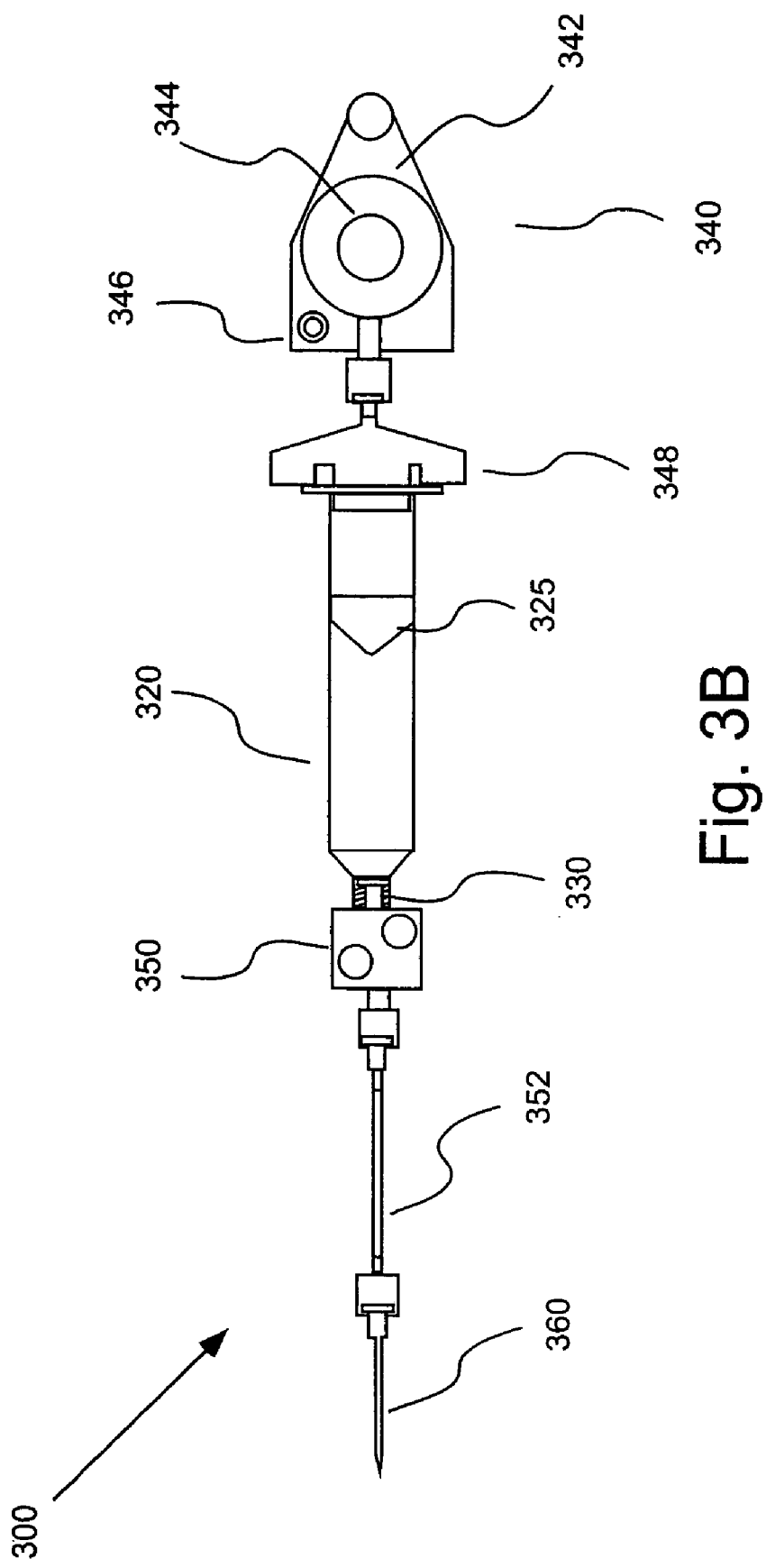
FIG. 3B illustrates the injection device of FIG. 3A in an assembled state.

FIGS. 3A and 3B illustrate another embodiment of an injection device 300 of the present invention. Injection device 300 includes a syringe 320 to which a pressurizing mechanism 340 is attached. Pressurizing mechanism 340 operates via release of a pressurizing gas (for example, carbon dioxide released by reaction of an acid such as citric acid with a base) using a principle similar to the operation of the SMARTDOSE® IV infusion drug delivery system available from PRO-MED AG of Linz, Austria. Although the SMARTDOSE system is not operable for use herein, the power/pressurizing mechanism used therein can be modified to create substantially higher pressures for use in the present invention. The use of gas generation to pressurize a fluid for injection is also disclosed, for example, in U.S. Pat. Nos. 6,413,238, 6,387, 228 and 5,588,556. The release of a gas such as carbon dioxide from a chamber 342 can be activated, for example, via actuation of a button 344. Flow of gas from pressurizing mechanism 340 (and thereby pressure) can be controlled, for example, via a control valve 346. A barrel adapter 348 connects pressurizing mechanism 340 to syringe 320 in which a reciprocating plunger 325 is slidably disposed.

Outlet 330 of syringe 320 is connected to an actuator 350. Actuator 350 can, for example, be a simple on/off type switching mechanism that either prevents flow or permits flow from syringe outlet 330 to tubing 352 (and therethrough to patient catheter 360). Even though activation button 344 of pressurizing mechanism 340 may have been previously activated, plunger 325 of syringe 320 will not move and no fluid will exit outlet 330 until actuator 350 is in the "on" state. As described above, actuator 350 can be a "wireless" actuator that is controlled from the MR control room via controller 370. Once actuator 350 is placed in the "on" state gas pressure from pressurizing mechanism 340 will cause plunger 325 to advance within syringe 320, thereby causing fluid to be injected into the patient through catheter 360. As described above, fluid flow rate/pressure can be controlled through a number of mechanisms. For example, the gas pressure created by pressurizing mechanism 340 can be adjusted (for example, via the size of pressurizing mechanism 340, via the type of reaction used and/or via the size/rating of pressure relief valve 346). As described above, an orifice of a predetermined size/diameter in the flow path can act to control flow rate/pressure. Moreover, the size/gauge of catheter 360 can be chosen to control flow rate/pressure.

FIGS. 3C and 3D illustrate embodiments of injection devices 300a and 300b of the present invention in which remote fluid pressure is used to inject a fluid into a patient. In FIG. 3C, injection device 300a includes a syringe or other fluid chamber 320a to which a pressurizing mechanism/actuator 340a is remotely attached via tubing 349a which passes through an end cap member 348a positioned on the rearward end of syringe 320a. In the embodiment of FIG. 3C, pressurizing mechanism 340a is a syringe 370a in which a plunger 380a is slidably disposed. When an operator forces plunger extension 390a forward (either manually or using a powered actuator—see, for example, FIG. 7 for an example of a remote actuator for a syringe), plunger 380a forces pressurized fluid (for example, saline) through tubing 349a and into an expandable bladder or balloon 325a positioned within syringe 320a.

Expansion of bladder 325a forces fluid contained within syringe 320a forward of bladder 325a out of outlet 330a of syringe 320a and into a patient (not shown in FIG. 3C) via optional tubing 352a and connected catheter 360a. Syringe 320a can, for example, be positioned inside the bore of an MRI device, while pressurizing mechanism/actuator 340a can be positioned outside of the bore of the MRI device.

In the embodiment of FIG. 3D, injection device 300b includes a syringe or other fluid chamber 320b to which a pressurizing mechanism/actuator 340b is remotely attached via tubing 349b which is in fluid connection with syringe 320b via an end cap member 348b positioned on the rearward end of syringe 320b. In the embodiment of FIG. 3D, pressurizing mechanism 340b is a syringe 370b in which a plunger 380b is slidably disposed. When an operator forces plunger extension 390b forward, plunger 380b forces pressurized fluid (for example, saline) through tubing 349b and into a volume of syringe 320b to the rear of a plunger 325b slidably disposed within syringe 320b.

Plunger 320b is thereby forced forward to force fluid contained within syringe 320b forward of plunger 325b out of outlet 330b of syringe 320b and into a patient (not shown in FIG. 3D) via optional tubing 352b and connected catheter 360b. As described above, syringe 320b can, for example, be positioned inside the bore of an MRI device, while pressurizing mechanism/actuator 340b can be positioned outside of the bore of the MRI device.

Figure 4A:
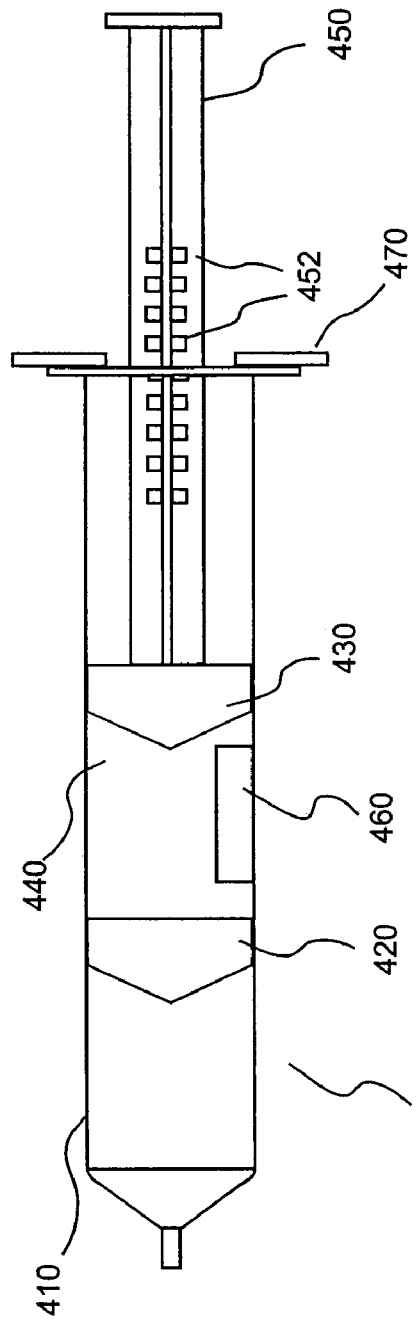
FIG. 4A illustrates another embodiment of an injection device of the present invention prior to actuation.
Figure 4B:
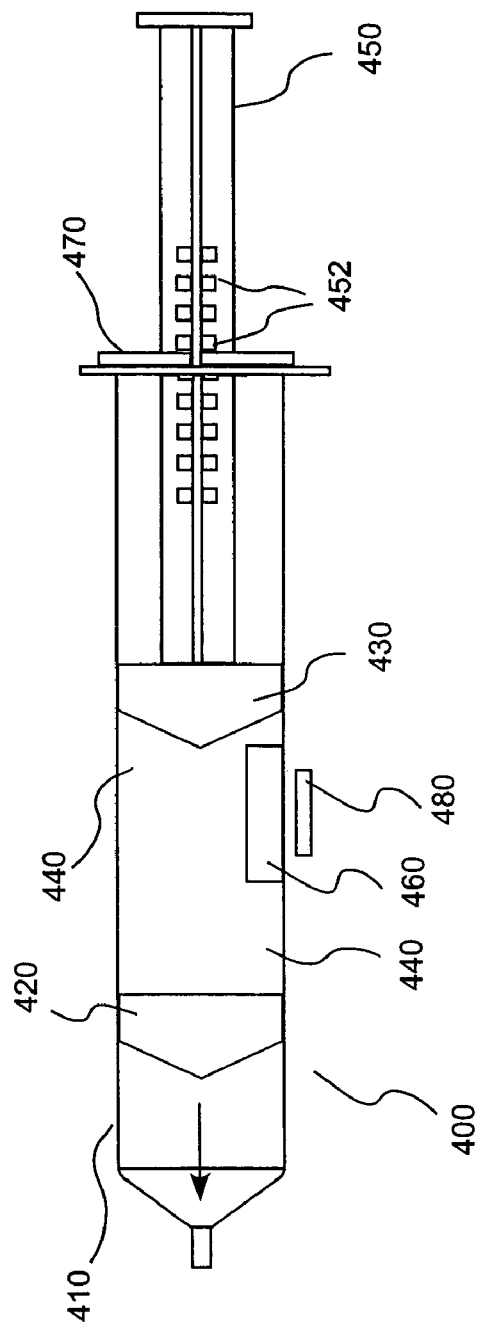
FIG. 4B illustrates the injection device of FIG. 4A after actuation.

FIGS. 4A and 4B illustrate another embodiment of an injection device 400 of the present invention. Injection device 400 is similar in operation to a syringe as commonly used to inject fluids into patients. In the embodiment of FIGS. 4A and 4B device 400 includes a syringe barrel 410 in which a first plunger 420 and a second plunger 430, spaced from first plunger 420 to create an intermediate region 440, are slidably disposed. A plunger extension 450 is operably connected to and extends rearward from second plunger 430.

Intermediate space or volume 440 can, for example, be filled with an incompressible fluid such as water. Intermediate volume 440 also preferably includes therein a mechanism 460 for applying force to first plunger 420 to inject fluid contained within syringe barrel 410 forward of first plunger 420. The pressurizing mechanism 460 can, for example, be a carbon dioxide generator (for example, a reactive mixture of an alkali metal carbonate and a weak organic acid).

During operation, second plunger 430 can be drawn rearward (which will cause first plunger 420 to also be drawn rearward) to draw an injection fluid into the volume of syringe barrel 410 forward of first plunger 420. Air can be expelled, from the volume of syringe barrel 410 forward of first plunger 420 by advancing plunger extension 450 forward, thereby advancing both second plunger 430 and first plunger 420 forward within syringe barrel 410. Device 400 is now primed and ready for use to inject fluid into a patient. At this point, the operator can lock the position of second plunger 430 within syringe barrel 410 by sliding abutment members 470 into abutting connection with flanges or tabs 452 formed on or attached to plunger extension 450. The pressurizing mechanism can be activated to, for example, create carbon dioxide and increase the pressure within intermediate volume 440. Once the controller (as described above) is activated, fluid will be forced from syringe barrel 410 in a controlled manner.

Activation of pressurizing mechanism 460 such as carbon dioxide generator can be accomplished in a wireless manner by, for example, using induction or magnetic energy applied across syringe barrel 410 via, for example, an actuating mechanism 480 placed in the vicinity of pressurizing mechanism 460 as illustrated in FIG. 4B.

Alternatively, as illustrated in FIG. 5A, a mechanical actuating mechanism such as a button 480' can be incorporated into plunger extension 450' to activate pressurizing mechanism 460'. Device 400' of FIG. 5A operates in generally a similar manner to device 400 of FIGS. 4A and 4B. Like components of device 400' are numbered similarly to corresponding components of device 400, with the addition of the designation "'".

FIG. 5B illustrates another embodiment of an injection device 400" of the present invention, which operates similarly to injection devices 400 and 400'. In the embodiment of FIG. 5B device 400" includes a syringe barrel 410" in which a first plunger 420" and a second plunger 430", spaced from first plunger 420" to create an intermediate region 440", are slidably disposed. A plunger extension 450" is operably connected to and extends rearward from second plunger 430".

Intermediate space or volume 440" can, for example, be filled with a fluid including an aqueous solution of acetic acid or citric acid. In this embodiment, plunger 430" can include a chamber 431" formed therein in which is positioned a pellet 460" of a compound such as an sodium carbonate or calcium carbonate that forms carbon dioxide when it react with acetic acid of citric acid. Chamber 431" is separated from intermediate volume 440" by a relatively thin membrane 436". A rearward end of chamber 431" is separated from a plunger extension/piston 450 by an elastomeric membrane or diaphragm 434". To activate syringe barrel 410", the operator rotates plunger extension 450" relative to syringe barrel 410. Threading 454" on a forward end of plunger extension 450" cooperates with threading 432" formed in a rearward end of plunger 430" to cause plunger extension 450" to move forward relative to plunger 430". A forward surface of plunger extension 450" deforms membrane 434", which forces pellet 460" forward to break through thin membrane 436" and come into contact with the fluid within intermediate volume 440". A reaction which releases carbon dioxide and increases the pressure within intermediate volume 440" is initiated, thereby applying force to first plunger 420" to inject fluid contained within syringe barrel 410" forward of first plunger 420". When plunger extension 450 is rotated as described above, tabs 452" can come into contact with a radially inward extending flange 470" positioned on a rearward end of syringe barrel 410" to prevent axial motion of plunger extension 450 relative to syringe barrel 410" as described in connection with the embodiment of FIGS. 4A through 5A.

FIGS. 6A through 6D illustrate another embodiment of an injection device 500 of the present invention that operates in a manner similar to the embodiments of FIGS. 4A through 5. In that regard, device 500 includes a syringe barrel 510 in which a first plunger 520 and a second plunger 530, spaced from first plunger 520 to create an intermediate region 540, are slidably disposed. A plunger extension 550 is operably connected to and extends rearward from second plunger 530.

As described above, intermediate space or volume 540 can, for example, be filled with an incompressible fluid such as water. Intermediate volume 440 also preferably includes therein a mechanism 560 for applying force to first plunger 520 to inject fluid contained within syringe barrel 510 forward of first plunger 520. Once again, pressurizing mechanism 560 can, for example, be a carbon dioxide generator.

Figure 6A:
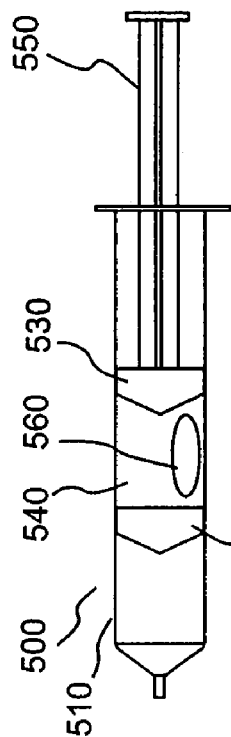
FIG. 6A illustrates another embodiment of an injection device of the present invention wherein a first plunger is in a position for loading of the syringe barrel.
Figure 6B:
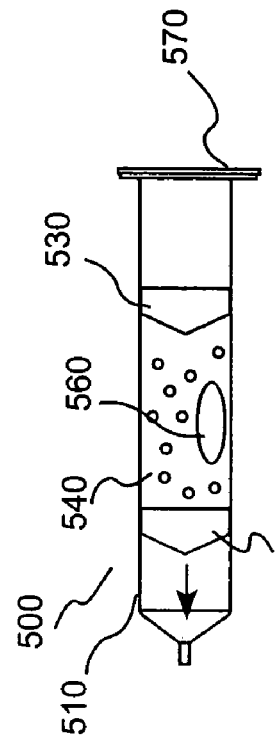
FIG. 6B illustrates the injection device of FIG. 6A wherein the plunger extension attached to the second plunger has been drawn rearward to load the syringe barrel.
Figure 6C:
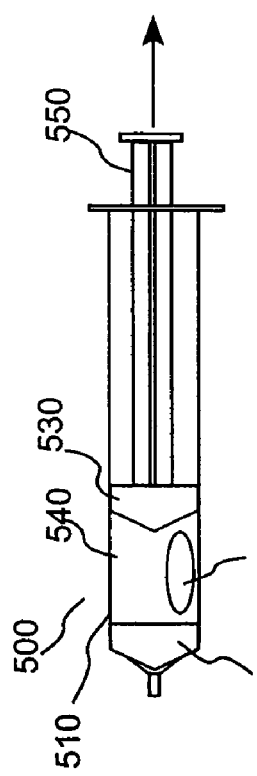
FIG. 6C illustrates the injection device of FIG. 6B wherein the plunger extension has been removed and the rear opening of the syringe has been sealed.
Figure 6D:
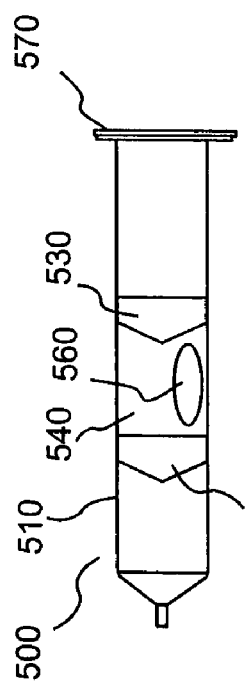
FIG. 6D illustrates the injection device of FIG. 6C after activation thereof to inject the fluid from within the syringe barrel.

During operation, second plunger 530 is drawn rearward, causing first plunger 520 to be drawn rearward, to draw injection fluid into the volume of syringe barrel 510 forward of first plunger 520 (see FIGS. 6A and 6B). Air can be expelled, from the volume of syringe barrel 510 forward of first plunger 520 by advancing plunger extension forward, thereby advancing both second plunger 530 and first plunger 520 forward within syringe barrel 510. At this point, the operator can, for example, remove plunger extension 550 from connection with second plunger 530 (via, for example, cooperating threading or a bayonet connection). The operator then can seal or cover the rear opening of syringe barrel 510 using a rearward member 570 as illustrated in FIG. 6C. Pressurizing mechanism 560 can be activated to, for example, create carbon dioxide and increase the pressure within intermediate volume 540. Second plunger 530 may move rearward within syringe barrel 510 until, for example, the pressure of the air compressed in the volume to the rear of second plunger 530 is equal to the pressure in intermediate volume 540 or until second plunger 530 contacts rearward member 570. Once the controller (as described above) is activated to place the actuator in the "on" state, fluid will be forced from syringe barrel 510 in a controlled manner.

It is not necessary to completely seal or cover the rearward end of syringe barrel 510. As long as second plunger 530" is prevented from exiting the rear of syringe barrel 510, injection device 500 will be operable. An abutment member that does not completely seal or cover the rear opening of syringe barrel 510, but which prevents second plunger 530 from exiting the rearward end of syringe barrel 510 thus can be used. It may not be necessary to remove plunger extension 550 from operative connection with second plunger 430 when using such an abutment member.

FIG. 7 illustrates an embodiment of hydraulically or pneumatically operated actuator 600 of the present invention, which can be used with any of the injection devices of the present invention or other injection devices. In the embodiment of FIG. 7, actuator 600 includes a syringe barrel that forms an actuating chamber 710, which is connected to a controller 800 (in the form of a syringe) via a length of flexible tubing 900. Actuating chamber 710 includes therein a valve mechanism 720.

Valve mechanism 720 is preferably in a normally closed state. Syringe 800 can, for example, be located outside of the bore of an MRI device while injection device 500 and actuator 600 are positioned within the bore of the MRI device. In one embodiment, syringe 800 is positioned within the control room of an MRI suite. In another embodiment, syringe 800 is positioned within the MRI room, but outside of the MRI bore. In this embodiment, a remote actuating device 1000 can be in communicative connection (via, for example, antenna 1100) with a control device 1200 located within the control room of the MRI suite. When an operator forces the plunger 810 of syringe 800 forward via plunger extension 820 either manually or through use of actuating device 1000, the resulting pressure increase within actuating syringe chamber 710 causes valve 720 to be in the "on" state and allow fluid to flow from injection device 500 (or other injection device) to a patient (not shown). Each of injection device 500 and actuator 600 can, for example, be placed in the bore of an MRI device (not shown in FIG. 7). Valve mechanism 720 can, for example, include an elastomeric cover or an elastomeric diaphragm 730 that is forced rearward when syringe 800 is activated to switch valve 720 from the "off" state to the "on" state. Valve 720 can, for example, be spring loaded in a closed position or in the "off" state using a non-ferromagnetic spring.

In the embodiments described above, the injection devices are particularly useful in MR procedures in which a single injection at a single flow rate is desired. However, as clear to one skilled in the art, the injection devices of the present invention are readily adaptable to procedures other than MR procedures in which much higher pressures/flow rates are used and in which it often is desirable to have timed phases in which, for example, one or more flow rates might occur. Multiple phase can, for example, be provided using multiple containers, multiple actuators, multiple pressurizing units, multiple orifices and/or one or more adjustable orifices.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A device for injection of a fluid into a patient, comprising:
   (a) a syringe configured to hold the fluid and defining an outlet through which the fluid can exit therefrom, the syringe having a plunger slidably disposed therein and being adapted to be placed in fluid connection with the patient such that no more than one foot of connective tubing is required between the syringe and an injection point on the patient;
   (b) a pressurizing mechanism comprising a vacuum drive in operative connection with the plunger of the syringe for pressurizing the fluid therein, the vacuum drive including:
      (i) a housing defining at least one chamber therein in which a sealing member is slidably disposed, the sealing member being configured to retract from a closed end of the at least one chamber to a position away from the closed end and configured to enable at least a partial vacuum to be internally developed within the at least one chamber as the sealing member is slidably drawn away from the closed end thereof; and
      (ii) a force transfer member, linked to the sealing member within the at least one chamber, to which the plunger of the syringe operatively links when the syringe is secured to the housing;
   (c) an actuator connected to the outlet of the syringe, the actuator being configured to switch between a first state in which the fluid is prevented from flowing through the outlet and a second state in which the fluid can flow through the outlet;
   (d) a controller configured to control the state of the actuator; and
   (e) a flow regulator configured to regulate the rate at which the fluid flows from the outlet and thus into the patient;
   such that, upon the at least partial vacuum being established within the at least one chamber and the syringe being secured to the housing, when the actuator is switched to the second state, the force transfer member receives a force caused by the at least partial vacuum pulling the sealing member towards the closed end of the at least one chamber and transfers the force to the plunger of the syringe thereby causing the fluid contained therein to be expelled from the outlet.

2. The device of claim 1 wherein a mechanism of the actuator comprises a rotory valve, a pinch valve with tubing, a ratchet valve, a fusible link, a trumpet valve, a port closing valve, a pump system or a drive system.

3. The device of claim 2 wherein the mechanism of the actuator is powered by a vacuum drive, a piezoelectric drive, an electric motor drive, a solenoid drive, an electro resistive pump, a charged ion pump, a magneto restrictive material, a TCAM device, a shape memory alloy material, a state transition, a bi-metallic material, an electro-active polymeric material or gravity.

4. The device of claim 1 wherein the controller is remote from the actuator.

5. The device of claim 1 wherein the controller is untethered from the actuator.

6. The device of claim 1 wherein the controller controls the state of the actuator via ultrasound, via a protocol of an imaging scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via optical light, via an RF signal, or via line power.

7. The device of claim 1 wherein the syringe, the pressurizing mechanism, the actuator and the flow regulator are MR compatible, thereby making the device suitable for use in or near the bore of an MR scanner.

8. The device of claim 1 wherein the flow regulator comprises a fluid path element having a known diameter.

9. The device of claim 1 wherein the flow regulator comprises a mechanism to control the pressure generated by the pressurizing mechanism, an orifice of selectable diameter, an adjustable orifice, or a catheter.

10. The device of claim 1, further comprising an attachment mechanism for attaching the device to the patient.

11. A system for use in magnetic resonance imaging, comprising: a magnetic resonance (MR) scanner defining a bore in which a patient is positioned for a scan; and a device for injection of a fluid into a patient, the device comprising:
(a) a syringe configured to hold the fluid and defining an outlet through which the fluid can exit therefrom, the syringe having a plunger slidably disposed therein and being configured to be placed in fluid connection with the patient;
(b) a pressurizing mechanism comprising a vacuum drive in operative connection with the plunger of the syringe for pressurizing the fluid therein, the vacuum drive including:
(i) a housing defining a chamber therein in which a sealing member is slidably disposed, the sealing member being configured to retract from a closed end of the chamber to a position away from the closed end and configured to enable a vacuum to be internally developed within the chamber as the sealing member is slidably drawn away from the closed end thereof; and
(ii) a force transfer member, linked to the sealing member within the chamber, to which the plunger of the syringe operatively links when the syringe is secured to the housing;
(c) an actuator connected to the outlet of the syringe, the actuator being switchable between a first state in which the fluid is prevented from flowing through the outlet and a second state in which the fluid can flow through the outlet;
(d) a controller configured to control the state of the actuator; and
(e) a flow regulator configured to regulate the rate at which the fluid flows from the outlet, wherein the syringe, the pressurizing mechanism, the actuator and the flow regulator are MR compatible, thereby making the device suitable for use in or near the bore of the MR scanner;
such that, upon the vacuum being established within the chamber and the syringe being secured to the housing, when the actuator is switched to the second state, the force transfer member receives a force caused by the vacuum pulling the sealing member towards the closed end of the chamber and transfers the force to the plunger of the syringe thereby causing the fluid contained therein to be expelled from the outlet.

12. The system of claim 11 wherein the syringe is removably secured to the housing.

13. The system of claim 11 wherein a mechanism of the actuator comprises a rotory valve, a pinch valve with tubing, a ratchet valve, a fusible link, a trumpet valve, a port closing valve, a pump system or a drive system.

14. The system of claim 13 wherein the mechanism of the actuator is powered by a vacuum drive, a piezoelectric drive, an electric motor drive, a solenoid drive, an electro resistive pump, an exigent pump, a magneto restrictive material, a TCAM device, a shape memory alloy material, a state transition, a bi-metallic material, an electro-active polymeric material or gravity.

15. The system of claim 11 wherein the controller is remote from the actuator.

16. The system of claim 11 wherein the controller is untethered from the actuator.

17. The system of claim 11 wherein the controller controls the state of the actuator via ultrasound, via a protocol of the MR scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via light control, via an RF signal, or via line power.

18. The system of claim 11 wherein the flow regulator comprises at least one of a mechanism to control the pressure generated by the pressurizing mechanism, a fluid path element of a known diameter, an orifice of selectable diameter, and an adjustable orifice.

19. The system of claim 18 wherein the flow regulator is a catheter.

20. The system of claim 11 wherein the device further comprises an attachment mechanism for attaching the device to the patient.

21. An injection device comprising:
(a) a syringe for injecting fluid into a patient, the syringe having a first plunger slideably disposed therein, a second plunger slidably disposed therein, an outlet at a forward end thereof and a plunger extension attached to a rearward end of the second plunger, the first plunger being spaced forward from the second plunger in the syringe to create an intermediate volume therebetween, the intermediate volume being filled with an incompressible fluid;
(b) a gas generating mechanism disposed within the intermediate volume; and
(c) an activating mechanism configured to activate the gas generating mechanism thereby enabling pressure to build within the intermediate volume;
such that advancement of the plunger extension in a forward direction forces both the second and the first plungers forward until the first plunger abuts against the forward end of the syringe and, upon connection of the outlet to a source of the fluid, subsequent retraction of the plunger extension forces both the second and first plungers rearward thereby drawing the fluid into the syringe forward of the first plunger and, upon readying the patient for injection with the syringe, activation of the gas generating mechanism while the second plunger is locked into a fixed position causes the fluid to be expelled from the outlet of the syringe by virtue of the pressure building up in the intermediate volume.

22. The injection device of claim 21 further including a rearward member for locking the second plunger into the fixed position and thus preventing retraction thereof after the gas generating mechanism has been activated.

23. An injection device comprising:
(a) a syringe for injecting fluid into a patient, the syringe having a first plunger slideably disposed therein, a second plunger slidably disposed therein, an outlet at a forward end thereof and a plunger extension attached to a rearward end of the second plunger, the first plunger being situated forward of the second plunger in the syringe;
(b) a gas generating mechanism disposed between the first and the second plungers;
(c) an activating mechanism configured to activate the gas generating mechanism thereby enabling pressure to build between the first and the second plungers; and
(d) means for locking the plunger extension and thus the second plunger attached thereto into a fixed position;
such that advancement of the plunger extension in a forward direction forces both the second and the first plungers forward until the first plunger abuts against the forward end of the syringe and, upon connection of the outlet to a source of the fluid, subsequent retraction of the plunger extension forces both the second and first plungers rearward thereby drawing the fluid into the syringe forward of the first plunger and, upon readying the patient for injection with the syringe and locking the second plunger into the fixed position using the means therefor, activation of the gas generating mechanism while the second plunger is so locked causes the fluid to be expelled from the outlet of the syringe by virtue of the pressure building up between the first and the second plungers.

24. The injection device of claim 23 wherein the gas generating mechanism includes:
   (a) an incompressible fluid including at least one of acetic acid and citric acid disposed between the first and the second plungers; and
   (b) at least one of sodium carbonate and calcium carbonate disposed within a chamber defined in the forward end of the second plunger and sealed therein by a thin breakable membrane.

25. The injection device of claim 24 wherein the activating mechanism includes:
   (a) a threaded bore defined through the second plunger and in communication with the chamber in which the at least one of the sodium carbonate and the calcium carbonate is disposed; and
   (b) the plunger extension having a threaded portion at the forward end thereof that is threadably engaged within the threaded bore by which the plunger extension is attached to the second plunger;
   whereby rotation of the plunger extension causes further threading of the plunger extension into the second plunger and the chamber defined therein so as to break the membrane and expose the at least one of the sodium carbonate and the calcium carbonate to the incompressible fluid and thereby cause gas to be formed by the combination thereof so as to build up the pressure between the first and the second plungers.

* * * * *

UNITED STATES PATENT AND TRADEMARK OFFICE
CERTIFICATE OF CORRECTION

PATENT NO. : 7,632,245 B1
APPLICATION NO. : 10/921083
DATED : December 15, 2009
INVENTOR(S) : Cowan et al.

It is certified that error appears in the above-identified patent and that said Letters Patent is hereby corrected as shown below:

ON THE TITLE PAGE,
In item [75], under "Inventors", in Column 1, Line 6, delete "Callan," and insert -- Callen, --, therefor.
On Page 2, in item (56), under "U.S. PATENT DOCUMENTS", in Column 1, Line 11, delete
"6,413,238 B1 7/2002 Maget" and insert -- 6,413,238 B1* 7/2002 Maget 604/132 --, therefor.

In Column 8, Line 64, delete "vaccuum" and insert -- vacuum --, therefor.
In Column 9, Line 19, delete "10" and insert -- 110 --.

Signed and Sealed this

Seventeenth Day of August, 2010

David J. Kappos
*Director of the United States Patent and Trademark Office*